(12) United States Patent
Yoshinaka et al.

(10) Patent No.: US 9,133,349 B2
(45) Date of Patent: Sep. 15, 2015

(54) ZINC OXIDE FILM-FORMING COMPOSITION, ZINC OXIDE FILM PRODUCTION METHOD, AND ZINC COMPOUND

(71) Applicant: Adeka Corporation, Tokyo (JP)

(72) Inventors: Atsuya Yoshinaka, Tokyo (JP); Tetsuji Abe, Tokyo (JP)

(73) Assignee: Adeka Corporation, Tokyo (JP)

( * ) Notice: Subject to any disclaimer, the term of this patent is extended or adjusted under 35 U.S.C. 154(b) by 0 days.

(21) Appl. No.: 13/961,124

(22) Filed: Aug. 7, 2013

(65) Prior Publication Data

US 2013/0323413 A1     Dec. 5, 2013

Related U.S. Application Data

(63) Continuation of application No. PCT/JP2012/050486, filed on Jan. 12, 2012.

(30) Foreign Application Priority Data

Mar. 9, 2011   (JP) .................. 2011-052024

(51) Int. Cl.
| | |
|---|---|
| C09D 5/24 | (2006.01) |
| C23C 14/08 | (2006.01) |
| C23C 18/12 | (2006.01) |
| C23C 18/42 | (2006.01) |
| C07C 211/65 | (2006.01) |
| C07F 3/06 | (2006.01) |
| C09D 1/00 | (2006.01) |

(52) U.S. Cl.
CPC ............. *C09D 5/24* (2013.01); *C07C 211/65* (2013.01); *C07F 3/06* (2013.01); *C09D 1/00* (2013.01); *C23C 14/086* (2013.01); *C23C 18/1216* (2013.01); *C23C 18/42* (2013.01)

(58) Field of Classification Search
CPC .. C23C 18/1216; C23C 14/086; C23C 14/12; C23C 14/228; C23C 18/44; C23C 18/42; C23C 22/02; C23C 22/76; C23C 22/77
USPC ....................................................... 106/1.29
See application file for complete search history.

(56) References Cited

U.S. PATENT DOCUMENTS 5,820,664 A * 10/1998 Gardiner et al. ......... 106/287.17
2007/0298190 A1  12/2007 Kobori et al.

FOREIGN PATENT DOCUMENTS

| CN | 101061062 A | 10/2007 |
|---|---|---|
| CN | 101696492 A | 4/2010 |
| EP | 1 993 122 A2 | 11/2008 |
| JP | 07-180060 A1 | 7/1995 |
| JP | 2004-022268 A1 | 1/2004 |
| KR | 10-2009-0131015 A | 12/2009 |
| WO | 2010/001949 A1 | 1/2010 |

OTHER PUBLICATIONS

Jong Pil Park, Sin Kyu Kim, Jae-Young Park, Kang Min Ok, and Il-Wun Shim, Preparation of ZnO Thin Films Using Zn/O-containing Single Precursor through MOCVD Method, pp. 114-118, 2009, vol. 30.*
NPL Preparation of ZnO Thin Films Using Zn/O-containing Single Precursor through MOCVD Method, Jong Pil Park, Sin Kyu Kim, Jae-Young Park, Kang Min Ok, and Il-Wun Shim. Bull. Korean Chem. Soc. 2009, vol. 30, No. 1.*
KR-10-2009-0131015 A—machine translation.*
International Search Report dated Mar. 19, 2012.
European Search Report (Application No. 12755681.9) dated Mar. 31, 2015.
Chinese Office Action (With EPO Machine English Translation), Chinese Application No. 201280012284.5, dated Mar. 6, 2015 (13 pages).

* cited by examiner

*Primary Examiner* — David Turocy
*Assistant Examiner* — Mohammad Mayy
(74) *Attorney, Agent, or Firm* — Burr & Brown, PLLC

(57) ABSTRACT

Disclosed are a composition for forming a zinc oxide-based film, said composition containing, as an essential component, a zinc compound represented by the following formula (1):

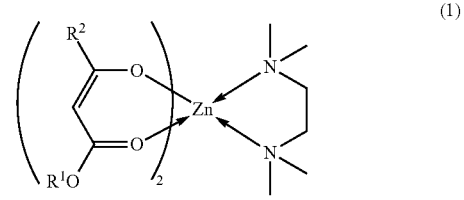

(1)

wherein $R^1$ and $R^2$ mutually independently represent an alkyl group having 1 to 4 carbon atoms, a process for producing the zinc oxide-based film, and the zinc compound. The composition makes it possible to form a high-quality zinc oxide-based film, which has transparency, homogeneity and electrical conductivity, at a low temperature of 300° C. or lower.

6 Claims, 3 Drawing Sheets

ZINC OXIDE FILM-FORMING COMPOSITION, ZINC OXIDE FILM PRODUCTION METHOD, AND ZINC COMPOUND

BACKGROUND OF THE INVENTION

1. Field of the Invention

This invention relates to a composition for forming zinc oxide-based films on various substrates, a process for producing a zinc oxide-based film, said process making use of the composition, and a zinc compound suitably usable in the composition.

2. Description of Related Art

Concerning zinc oxide-based films, a variety of studies are under way for applications as electrically conductive (hereinafter referred to simply as "conductive") transparent films, electrode materials, and semiconductor materials. Reported as processes for forming a zinc oxide-based film by using a zinc-oxide precursor compound include vapor-phase processes, such as CVD process and ALD process, that bring vaporized gas of a precursor compound into contact with a substrate (base material); and liquid-phase processes, such as MOD process and sol-gel process, that bring a solution or dispersion of a precursor compound into contact with a substrate.

Zinc compounds useful as zinc-oxide precursor compounds in these processes include alkoxides, β-diketone complexes, organic acid metal salts, zinc alkyls, inorganic salts, and the like. These precursor compounds are converted into zinc oxide through reactions under heat and/or with oxidizing agents.

For example, Patent Document 1 discloses a process for producing a thin zinc oxide film, which comprises bringing a suspension, in which a powder or fine particles of a zinc compound is or are dispersed, into contact with a surface of a substrate, and then thermally decomposing the zinc compound to convert the same into zinc oxide. As such zinc compounds, zinc acetate, zinc acetylacetonate, zinc oxalate, and zinc lactate are disclosed.

Patent Document 2, on the other hand, discloses a method for producing a transparent conductive film by bringing gas of an organic metal compound, said gas having been brought into a plasma state, into contact with a substrate under atmospheric pressure or a pressure around atmospheric pressure. In Patent Document 2, zinc oxide is exemplified as a transparent conductive film, and ethyl acetoacetate is exemplified as a ligand for forming an organic metal. Further, zinc acetylacetonate is exemplified as a zinc compound.

When forming a zinc oxide-based film by using a precursor compound, a temperature that is needed to convert the precursor compound into a zinc oxide-based film of quality sufficient to exhibit an expected function is generally considered to be 350° C. or higher. It is, however, desired to permit the conversion into such a zinc oxide-based film at a lower temperature from the standpoint of the adaptability to a resin substrate, a reduction in damage to a substrate, and the like. There is, accordingly, an outstanding desire for the development of a processor method for producing a zinc oxide-based film at a lower film-forming temperature than before.

PRIOR ART DOCUMENTS

Patent Documents

Patent Document 1: JP-A-7-180060
Patent Document 2: JP-A-2004-22268

SUMMARY OF THE INVENTION

Problem to be Solved by the Invention

With the foregoing problem of the conventional technologies in view, objects of the present invention are to provide a composition for forming a zinc oxide-based film, which makes it possible to form at a low temperature of 300° C. or lower a high-quality zinc oxide-based film having transparency, homogeneity and conductivity, and a zinc compound useful in the composition. A further object of the present invention is to provide a process for producing a zinc oxide-based film, which makes it possible to format a low temperature of 300° C. or lower a high-quality zinc oxide-based film having transparency, homogeneity and conductivity.

Means for Solving the Problem

As a result of an enthusiastic study, the present inventors have found that the use of a zinc compound having a specific structure can achieve the above-described objects, leading to the completion of the present invention. Described specifically, according to the present invention, there is provided a composition for forming a zinc oxide-based film, which comprises, as an essential component, a zinc compound represented by the following formula (1):

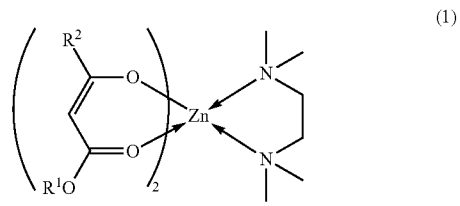

wherein $R^1$ and $R^2$ mutually independently represent an alkyl group having 1 to 4 carbon atoms.

In the present invention, $R^1$ and $R^2$ in the formula (1) may each preferably be a methyl group.

According to the present invention, there is also provided a process for producing a zinc oxide-based film, which comprises the following steps:

applying the above-mentioned composition to a substrate to form a coating layer, and treating the coating layer at 150 to 300° C. to convert the same into a film.

According to the present invention, there is also provided a zinc compound represented by the following formula (2):

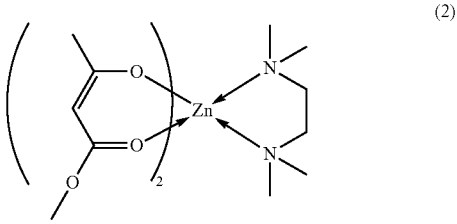

(2)

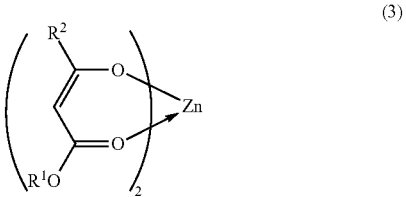

(3)

wherein $R^1$ and $R^2$ mutually independently represent an alkyl group having 1 to 4 carbon atoms.

In the composition according to the present invention, one or more optional components other than the specific zinc compound as an essential component may also be contained. Typical examples of the composition according to the present invention include:

(a) a composition containing the zinc compound represented by the formula (1) and an organic solvent in which the zinc compound is dissolved or dispersed;

(b) a composition containing the zinc compound represented by the formula (1), N,N,N',N'-tetramethylethylenediamine, and an organic solvent in which these components are dissolved or dispersed; and the like.

When the hydrate of a zinc complex of an acetoacetate ester (zinc material) and N,N,N',N'-tetramethylethylenediamine are reacted in a desired organic solvent, the water of hydration derived from the zinc material is contained in the resulting composition. This water of hydration may be removed or may be left unremoved from the resulting composition. When N,N,N',N'-tetramethylethylenediamine is reacted in excess to the zinc material, the excessive amount of N,N,N',N'-tetramethylethylenediamine is contained in the resulting composition. From the resulting composition, this excessive amount of N,N,N',N'-tetramethylethylenediamine maybe removed or may be left unremoved.

It is preferred to contain an adequate amount of N,N,N',N'-tetramethylethylenediamine in the composition according to the present invention, because the composition is provided with better stability and the resulting film is provided with improved quality (transparency and conductivity in the case of a zinc oxide film).

In the composition according to the present invention, an organic solvent is generally contained as a solvent or dispersion medium. This organic solvent may be either a single solvent or a mixed solvent. As organic solvents, alcohol solvents, diol solvents, ketone solvents, ester solvents, ether solvents, aliphatic or alicyclic hydrocarbon solvents, aromatic hydrocarbon solvents, cyano-containing hydrocarbon solvents, and other solvents can be mentioned.

Specific examples of the alcohol solvents include methanol, ethanol, propanol, isopropanol, 1-butanol, isobutanol, 2-butanol, tertiary butanol, pentanol, isopentanol, 2-pentanol, neopentanol, tertiary pentanol, hexanol, 2-hexanol, heptanol, 2-heptanol, octanol, 2-ethylhexanol, 2-octanol, cyclopentanol, cyclohexanol, cycloheptanol, methylcyclopentanol, methylcyclohexanol, methylcycloheptanol, benzyl alcohol, 2-methoxyethyl alcohol, 2-butoxyethyl alcohol, 2-(2-methoxyethoxy)ethanol, 1-methoxy-2-propanol, 2-(N,N-dimethylamino)ethanol, 3-(N,N-dimethylamino)propanol, and the like.

As the diol solvents, ethylene glycol, propylene glycol, 1,2-butanediol, 1,3-butanediol, 1,4-butanediol, 1,5-pentanediol, neopentyl glycol, isoprene glycol (3-methyl-1,3-butanediol), 1,2-hexanediol, 1,6-hexanediol, 3-methyl-1,5-pentanediol, 1,2-octanediol, octanediol (2-ethyl-1,3-

Advantageous Effects of the Invention

The use of the composition and zinc compound according to the present invention makes it possible to form, at a low temperature of 300° C. or lower, a high-quality zinc oxide-based film having transparency, homogeneity and conductivity. Further, according to the production process of the present invention, a high-quality zinc oxide-based film having transparency, homogeneity and conductivity can be formed at a low temperature of 300° C. or lower.

DETAILED DESCRIPTION OF THE INVENTION

Figure 1:
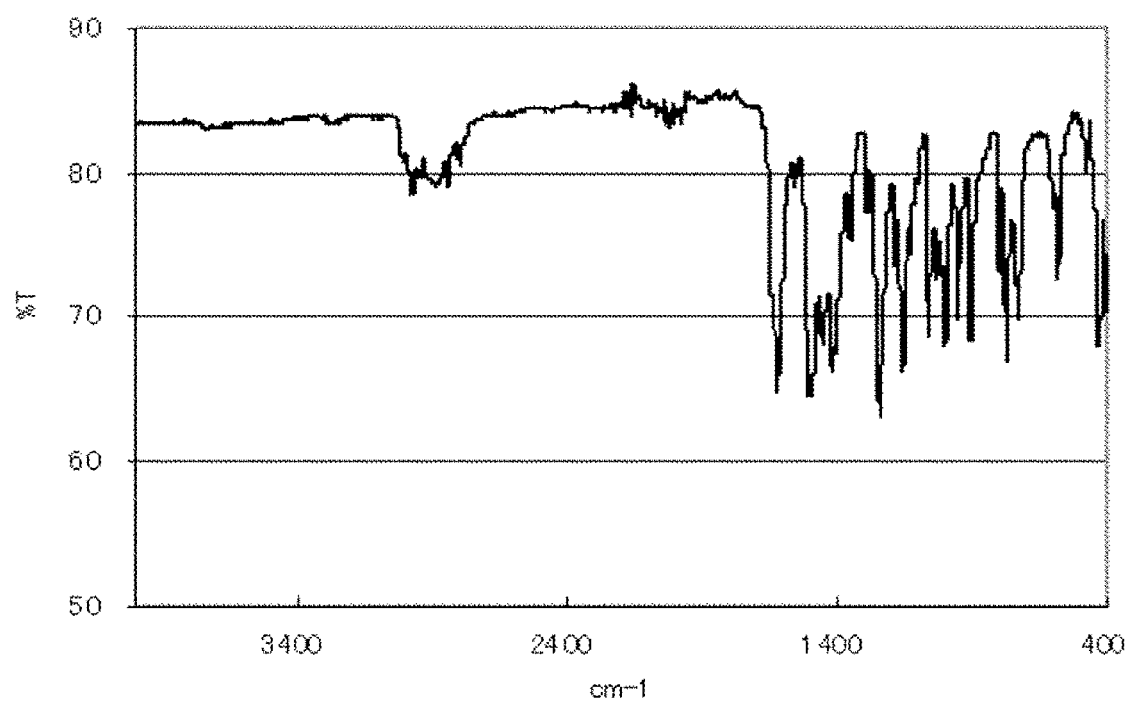
FIG. 1 is an IR chart of the zinc compound represented by the formula (2).

A description will hereinafter be made about the composition according to the present invention for forming a zinc oxide-based film. The composition according to the present invention contains as an essential component the zinc compound represented by the above-described formula (1). This zinc compound can function as a zinc oxide precursor compound. Specific examples of the alkyl group represented by $R^1$ and $R^2$ and having 1 to 4 carbon atoms in the formula (1) include methyl, ethyl, propyl, isopropyl, butyl, 2-butyl, isobutyl, t-butyl, and the like. $R^1$ may preferably be a methyl group as its raw material is economical. On the other hand, $R^2$ may preferably be a methyl group or ethyl group, with a methyl group being more preferred, because the corresponding zinc compound has good solubility in various organic solvents and can afford a stable composition.

Among zinc compounds represented by the formula (1), the most preferred is the zinc compound represented by the above-described formula (2). It is to be noted that the zinc compound represented by the above-described formula (2) is a novel compound.

The zinc compound contained as an essential component in the composition according to the present invention can be prepared, for example, by mixing a zinc complex of an acylacetate ester, as represented by the below-described formula (3), or a hydrate thereof with N,N,N',N'-tetramethylethylenediamine. The zinc compound represented by the formula (2) can be obtained, for example, by stirring a zinc complex (hydrate) of methyl acetoacetate and N,N,N',N'-tetramethylethylenediamine at room temperature or under heating in an organic solvent.

hexanediol), 2-butyl-2-ethyl-1,3-propanediol, 2,5-dimethyl-2,5-hexanediol, 1,2-cyclohexanediol, 1,4-cylohexanediol, 1,4-cyclohexanedimethanol, and the like can be mentioned.

As the ketone solvents, acetone, ethyl methyl ketone, methyl butyl ketone, methyl isobutyl ketone, ethyl butyl ketone, dipropyl ketone, diisobutyl ketone, methyl amyl ketone, cyclohexanone, methylcyclohexanone, and the like can be mentioned.

As the ester solvents, methyl formate, ethyl formate, methyl acetate, ethyl acetate, isopropyl acetate, butyl acetate, isobutyl acetate, secondary butyl acetate, tertiary butyl acetate, amyl acetate, isoamyl acetate, tertiary amyl acetate, phenyl acetate, methyl propionate, ethyl propionate, isopropyl propionate, butyl propionate, isobutyl propionate, secondary butyl propionate, tertiary butyl propionate, amyl propionate, isoamyl propionate, tertiary amyl propionate, phenylpropionate, methyl 2-ethylhexanoate, ethyl 2-ethylhexanoate, propyl 2-ethylhexanoate, isopropyl 2-ethylhexanoate, butyl 2-ethylhexanoate, methyl lactate, ethyl lactate, methyl methoxypropionate, methyl ethoxypropionate, ethyl methoxypropionate, ethyl ethoxypropionate, ethylene glycol monomethyl ether acetate, diethylene glycol monomethyl ether acetate, ethylene glycol monoethyl ether acetate, ethylene glycol monopropyl ether acetate, ethylene glycol monoisopropyl ether acetate, ethylene glycol monobutyl ether acetate, ethylene glycol monosecondary butyl ether acetate, ethylene glycol monoisobutyl ether acetate, ethylene glycol monotertiary butyl ether acetate, propylene glycol monomethyl ether acetate, propylene glycol monoethyl ether acetate, propylene glycol monopropyl ether acetate, propylene glycol monoisopropyl ether acetate, propylene glycol monobutyl ether acetate, propylene glycol monosecondary butyl ether acetate, propylene glycol monoisobutyl ether acetate, propylene glycol monotertiary butyl ether acetate, butylene glycol monomethyl ether acetate, butylene glycol monoethyl ether acetate, butylene glycol monopropyl ether acetate, butylene glycol monoisopropyl ether acetate, butylene glycol monobutyl ether acetate, butylene glycol monosecondary butyl ether acetate, butylene glycol monoisobutyl ether acetate, butylene glycol monotertiary butyl ether acetate, methyl acetoacetate, ethyl acetoacetate, methyl oxobutanoate, ethyl oxobutanoate, γ-butyrolactone, δ-valerolactone, and the like can be mentioned.

As the ether solvents, tetrahydrofuran, tetrahydropyran, morpholine, ethylene glycol dimethyl ether, diethylene glycol dimethyl ether, triethylene glycol dimethyl ether, dibutyl ether, diethyl ether, dioxane, and the like can be mentioned.

As the aliphatic or alicyclic hydrocarbon solvents, pentane, hexane, cyclohexane, methylcyclohexane, dimethylcyclohexane, ethylcyclohexane, heptanes, octane, decaline, solvent naphtha, and the like can be mentioned.

As the aromatic hydrocarbon solvents, benzene, toluene, ethylbenzene, xylene, mesitylene, diethylbenzene, cumene, isobutylbenzene, cumene, tetralin, and the like can be mentioned.

As the cyano-containing hydrocarbon solvents, 1-cyanopropane, 1-cyanobutane, 1-cyanohexane, cyanocyclohexane, cyanobenzene, 1,3-dicyanopropane, 1,4-dicyanobutane, 1,6-dicyanohexane, 1,4-dicyanocyclohexane, 1,4-dicyanobenzene, and the like can be mentioned.

As the other organic solvents, N-methyl-2-pyrrolidone, dimethyl sulfoxide, dimethyl formamide, and the like can be mentioned.

Among the above-described organic solvents, the alcohol solvents and ester solvents are preferred, as they are economical, show sufficient solubility for the zinc compound, and show good coating properties as coating solvents for various substrates such as silicon substrates, metal substrates, ceramic substrates, glass substrates, and resin substrates. When a mixed solvent is used, one containing at least one of an alcohol solvent and an ester solvent at 50 mass % or higher is more preferred. An organic solvent having a boiling point lower than the conversion temperature into a film is preferred, and an organic solvent having a boiling point of 150° C. or lower is more preferred.

A preferred embodiment of the composition according to the present invention may be a solution in which the zinc compound represented by the formula (1), N,N,N',N'-tetramethylethylenediamine and an organic solvent are contained as essential components and the zinc compound is dissolved. The zinc compound in the composition may preferably be at such a concentration that the composition remains as a stable solution. Described specifically, the content of the zinc compound in the composition may preferably be 0.01 to 0.1 mol/L. On the other hand, the amount of N,N,N',N'-tetramethylethylenediamine contained in the composition may preferably be 2 to 20 molar (mol/L) times of the zinc compound. The organic solvent may preferably be an ester solvent and/or alcohol solvent having a boiling point of 150° C. or lower.

In the composition according to the present invention, one or more components other than the above-mentioned components, which may hereinafter be referred to simply as "such other components", may be contained, as needed, to an extent that does not impair the advantageous effects of the present invention. "Such other components" can include additives capable of providing the composition with improved stability and coating properties, such as antigeling agents, solubilizing agents, defoaming agents, thickening agents, thixotropic agents, and leveling agents; and film-forming aids such as reaction catalysts, reaction aids, and crosslinking aids. The contents of "such other components" in the composition may each be preferably 10 mass % or lower, with 5 mass % or lower being more preferred.

For example, as a solubilizing agent for the zinc compound represented by the formula (1), the same acylacetate ester as the ligand in the zinc compound is preferred. The content of the acylacetate ester which may be contained in the composition may be 0.05 to 5 mass %. If the content of the acylacetate ester is lower than 0.05 mass %, its effects as a solubilizing agent may not be obtained. Even if the content of the acylacetate ester is set higher than 5 mass %, on the other hand, its effects as a solubilizing agent are not improved particularly but such an excessively high content may rather become uneconomical.

In the composition, an oxidizing agent which can convert the zinc compound as a precursor compound into zinc oxide may also be contained preferably. As the oxidizing agent, water is suited. Water acts upon the conversion of the zinc compound into zinc oxide, and contributes to providing the resulting zinc oxide-based film with higher quality. The content of water in the composition may preferably be 1 to 10 mass %. A water content lower than 1 mass % may not bring about the effect which would otherwise be available from the use of water. A water content higher than 10 mass %, on the other hand, renders the zinc compound prone to decomposition, and may hence become as a cause of a deterioration, such as gelation or solid formation, of the composition. Water may be added beforehand in an amount as needed in the composition, or may be added shortly before the production of a zinc oxide-based film.

A description will next be made about the process according to the present invention for the production of the zinc oxide-based film. The production process according to the present invention can effectively exhibit the above-mentioned characteristics of the composition. Described specifically, the production process according to the present invention includes the following steps: (1) applying the above-mentioned composition to a substrate such that a coating layer is formed (hereinafter called "the coating step"), and (2) treating the thus-formed coating layer at 150 to 300° C. to convert the same into a film (hereinafter called "the conversion-into-film step").

As a coating method of the composition in the coating step, spin coating, dip coating, spray coating, mist coating, flow coating, curtain coating, roll coating, knife coating, bar coating, screen printing, brush coating, or the like can be mentioned. No particular limitation is imposed on the substrate on which the composition is to be coated, but an inorganic substrate of glass, silicon or the like, a resin substrate of a polyimide, a polycarbonate, polyethylene terephtharate, polyethylene naphthalate or the like, or the like can be mentioned.

The coating layer formed on the substrate is treated at 150 to 300° C., preferably 200 to 300° C. to oxidize the zinc compound such that the zinc oxide-based film is formed. It is to be noted that the composition may be treated at 150 to 300° C. after its coating or may be treated at 150 to 300° C. concurrently with its coating. In other words, the coating step and conversion-into-film step may be conducted substantially at the same time. For conducting the treatment at 150 to 300° C. concurrently with the coating of the composition, it is possible, for example, that the substrate may be heated beforehand to a desired conversion temperature and the composition may be applied to the substrate. Such a method can be applied to spray coating or mist coating.

As an atmosphere of the conversion-into-film step, an oxidizing atmosphere, in which an oxidizing substance such as oxygen, ozone, nitrogen dioxide, nitrogen monoxide, water vapor, hydrogen peroxide, formic acid, acetic acid or acetic anhydride exists, is preferred. To control the oxidizing atmosphere, an inert gas may be used as a diluent gas.

After the coating of the composition, a drying step may preferably be included to vaporize components of low boiling point such as an organic solvent. Further, subsequent to the conversion into the film, annealing treatment may be conducted under an inert atmosphere, oxidizing atmosphere or reducing atmosphere to form a zinc oxide-based film of good quality. The temperature of the annealing treatment may be generally 150 to 400° C., preferably 150 to 300° C.

To provide the resulting zinc oxide-based film with a required thickness, the coating step and conversion-into-film step can be repeated a plurality of times. For example, it is possible to repeat from the coating step to the conversion-into-film step a plurality of time, or to repeat the coating step and the drying step a plurality of times, respectively. Moreover, energy other than heat, such as a plasma or one of various radiations, maybe applied or irradiated in each of these steps.

In the present invention, it is possible to form a zinc oxide-based film (thin film) capable of exhibiting desired characteristics, such as a film of a zinc oxide ceramic, a film of a composite oxide of zinc oxide and an element other than zinc, or a composite film of zinc oxide and an element other than zinc, by incorporating a precursor of a still further component in the composition, selecting suitable conditions for each step, or using a reactive gas in each step.

Examples of the zinc oxide-based film (thin film) to be produced include films of zinc oxide, zinc-indium complex oxide, lead-zinc complex oxide, lead-zinc-niobium complex oxide, bismuth-zinc-niobium complex oxide, barium-zinc-tantalum complex oxide, tin-zinc complex oxide, lithium-added zinc oxide, zinc-added ferrite, and the like. Examples of applications of these zinc oxide-based films (thin films) include semiconductors, transparent conductors, light emitters, fluorescent emitters, photocatalysts, magnets, conductors, electrodes, high dielectrics, ferroelectrics, piezoelectrics, microwave dielectrics, optical waveguides, optical amplifiers, optical switches, electromagnetic shields, solar cells, and the like.

EXAMPLES

The present invention will hereinafter be described in further detail based on examples. It should, however, be borne in mind that the present invention is by no means limited by the following examples.

(1) Production of Zinc Compound Represented by the Formula (2)

Example 1

Figure 2:
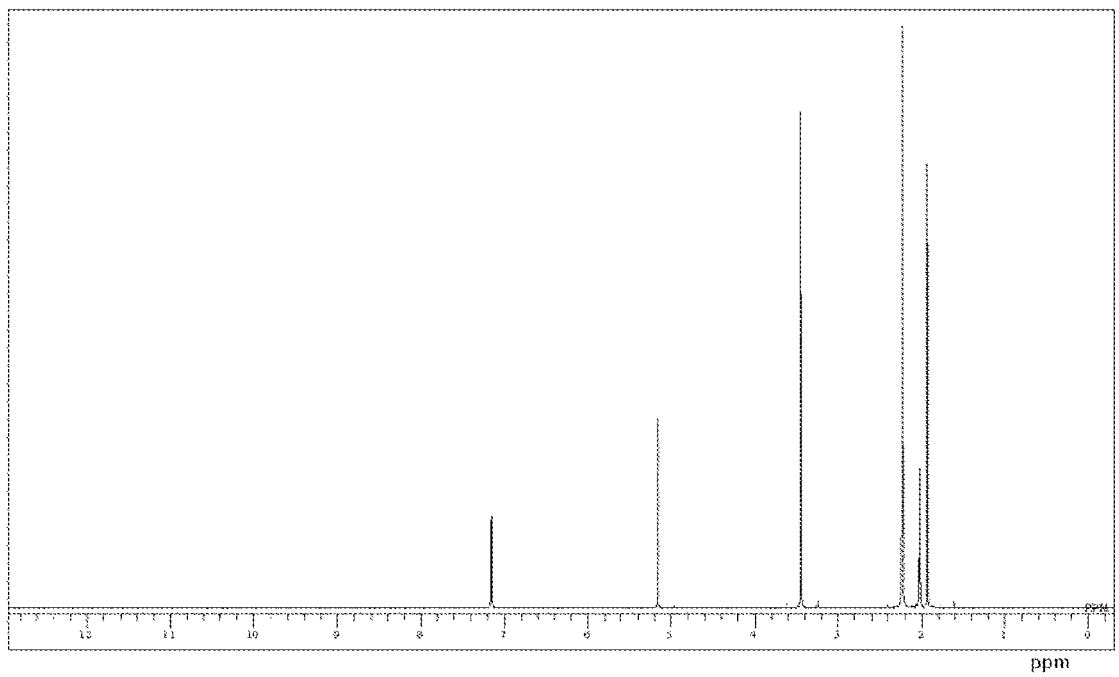
FIG. 2 is a $^1$H-NMR chart of the zinc compound represented by the formula (2).
Figure 3:
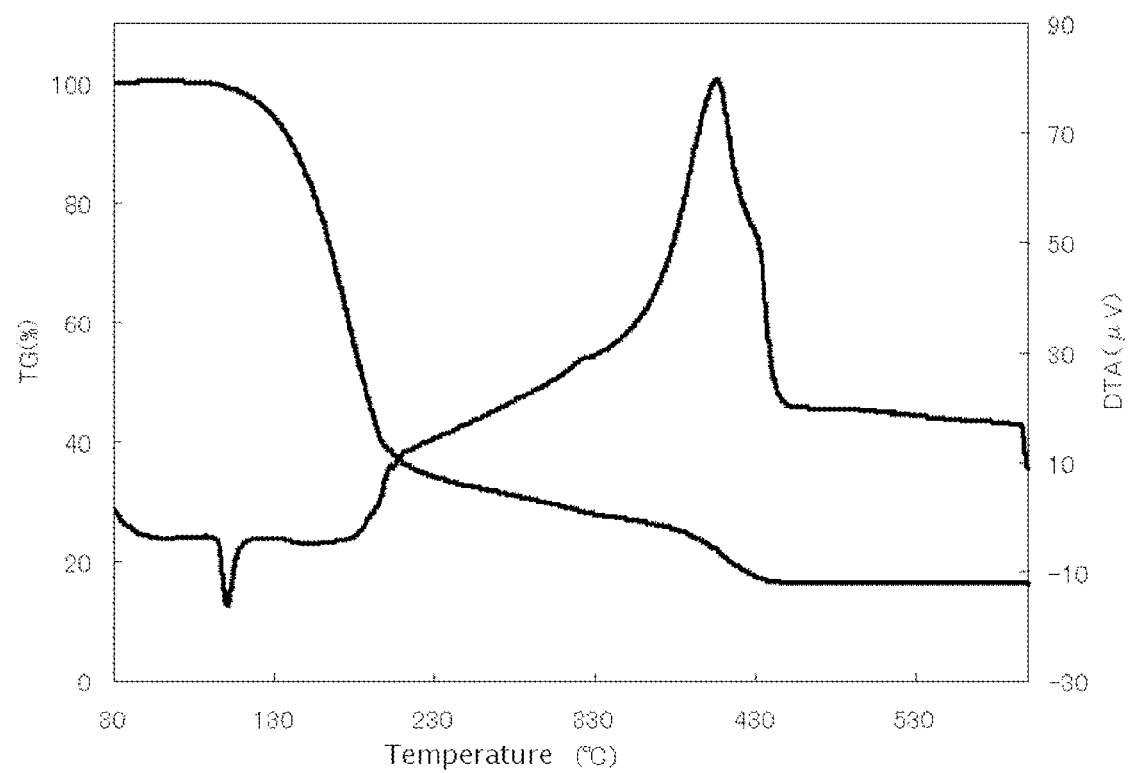
FIG. 3 is a TG-DTA chart of the zinc compound represented by the formula (2).

A reaction mixture, which had been obtained by mixing zinc chloride (1 molar parts), sodium methylate (2 molar parts) and methanol (8 molar times of the zinc chloride), was stirred at room temperature for 30 minutes. Precipitated sodium chloride was filtered off. The thus-obtained filtrate was added to a solution that contained methyl acetoacetate (2 molar parts) and methanol (3 molar times of the methyl acetoacetate), followed by stirring at room temperature for 30 minutes. After precipitated crystals were collected by filtration, the crystals were washed with methanol and dried to obtain a methyl acetoacetate complex of zinc with a yield of 95% as an intermediate. That intermediate (1 molar parts) and N,N,N',N'-tetramethylethylenediamine (1 molar parts) were added to hexane (1 molar times of the intermediate), followed by stirring for 1 hour under heating and reflux. The resulting solution was filtered, followed by recrystallization treatment at −30° C. to obtain the title compound, that is, the zinc compound represented by the formula (2) (white crystals) with a yield of 97%. On the white crystals so obtained, IR, $^1$H-NMR and TG-DTA were measured. The resulting IR, $^1$H-NMR and TG-DTA charts are shown in FIGS. 1, 2 and 3, respectively. It is to be noted that the measurement conditions were as described hereinafter.

<IR Measurement>

Measurement system: "Nicolet 6700" (trade name, manufactured by Thermo Fisher Scientific Inc.).

<$^1$H-NMR Measurement>

Measurement system: "JNM-ECA 400" (trade name, manufactured by JEOL Ltd.), frequency: 400 MHz, solvent: heavy benzene.

<TG-DTA>

Measurement system: "EXSTRA6000" (trade name, manufactured by SII Nano Technology Inc.), sample amount: 6 mg, air: 300 mL/mL, ramp-up rate: 10° C./min, reference: alumina.

(2) Preparation of Composition for Forming Zinc Oxide-Based Film

Example 2

The zinc compound represented by the formula (2) and obtained in Example 1 was dissolved in methyl acetate to prepare a composition (Example 2) for forming a zinc oxide-based film. It is to be noted that the concentration of the zinc compound represented by the formula (2) was set at 0.05 mol/L.

Examples 3 to 9, Comparative Examples 1 to 10

Compositions (Examples 3 to 9 and Comparative Examples 1 to 10) for forming a zinc oxide-based films, respectively, were prepared by separately mixing the corresponding components shown in Table 1. The zinc component represented by the formula (4) and the zinc component represented by the formula (5) are shown below.

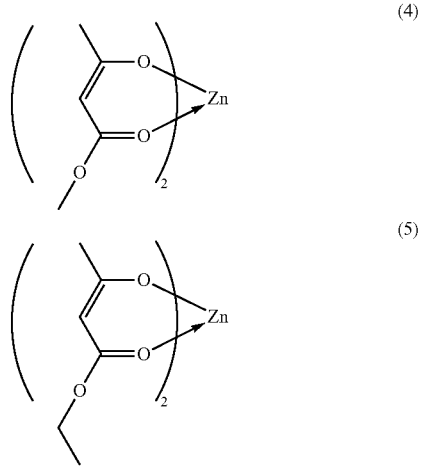

The spray volume per stroke was set at 0.1 mL, and the composition was repeatedly sprayed 200 times to apply it as much as 20 mL in total. After the spraying, the glass substrate was maintained at 200° C. for 30 minutes to form a film so that a filmed glass substrate was obtained.

The resultant filmed glass substrate was visually observed to evaluate the homogeneity of the formed film. The evaluation results are shown in Tables 2 and 3. As evaluation standards, one having irregularities on the coating film is indicated as "irregular", one containing agglomerates is indicated as "agglomerated", and homogeneous one is indicated as "homogeneous". Further, the composition failed to obtain a film is indicated as "no film".

Further, the transparency and conductivity of each formed film were also evaluated. The transparency was evaluated by using a turbidity meter ("NDH2000", trade name, manufactured by Nippon Denshoku Industries Co., Ltd.) and measuring the total light transmittance under a D65 light source. On the other hand, the conductivity was evaluated by using "Loresta-EP MCP-T360" (trade name, manufactured by Mitsubishi Chemical Corporation) and measuring the volume resistivity according to the four-point probe method. It is to be noted that the volume resistivity was measured at desired several measuring points and was expressed in terms of an average value. One having a measurement value greater than $10^7$ Ω·cm, measurement limit, is indicated as "∞". The measurement results of transmittance and resistivity are shown in Tables 2 and 3.

TABLE 1

| | Zinc component | | Components | | | | |
|---|---|---|---|---|---|---|---|
| | Kind | Conc. (mol/L) | Kind | Conc. (mass %) | Kind | Conc. (mol/L) | Organic solvent |
| Ex. 3 | Formula (4) | 0.05 | TMEDA[2] | 2 | — | — | Methyl acetate |
| Ex. 4 | Formula (4) | 0.05 | TMEDA | 10 | — | — | Methyl acetate |
| Ex. 5 | Formula (4) | 0.05 | TMEDA | 20 | — | — | Methyl acetate |
| Ex. 6 | Formula (5) | 0.05 | TMEDA | 10 | — | — | Methyl acetate |
| Ex. 7 | Formula (4) | 0.05 | TMEDA | 10 | Methyl acetoacetate | 1 | Methyl acetate |
| Ex. 8 | Formula (4) | 0.05 | TMEDA | 10 | Methyl acetoacetate | 5 | Methyl acetate |
| Ex. 9 | Formula (4) | 0.05 | TMEDA | 10 | Methyl acetoacetate | 1 | Methanol |
| Comp. Ex. 1 | Formula (4) | 0.05 | — | — | — | — | Methyl acetate |
| Comp. Ex. 2 | Formula (4) | 0.05 | TEA[3] | 10 | — | — | Methyl acetate |
| Comp. Ex. 3 | Formula (4) | 0.05 | EDA[4] | 10 | — | — | Methyl acetate |
| Comp. Ex. 4 | Formula (4) | 0.05 | EA[5] | 10 | — | — | Methyl acetate |
| Comp. Ex. 5 | Formula (4) | 0.05 | 2-MEA[6] | 10 | — | — | Methyl acetate |
| Comp. Ex. 6 | Formula (4) | 0.05 | N-MEA[7] | 10 | — | — | Methyl acetate |
| Comp. Ex. 7 | Formula (4) | 0.05 | DMEA[8] | 10 | — | — | Methyl acetate |
| Comp. Ex. 8 | Formula (4) | 0.05 | EGDME[9] | 10 | — | — | Methyl acetate |
| Comp. Ex. 9 | Formula (4) | 0.05 | 2-ME[10] | 10 | — | — | Methyl acetate |
| Comp. Ex. 10 | BPD-Zn[1] | 0.05 | TMEDA | 10 | — | — | Methanol |

[1] bis(pentane-2,5-dionato)zinc,
[2] N,N,N',N'-tetramethylethylenediamine,
[3] triethylamine,
[4] ethylenediamine,
[5] ethanolamine,
[6] 2-methoxyethylamine,
[7] N-methylethanolamine,
[8] N,N-dimethylethanolamine,
[9] ethylene glycol dimethyl ether,
[10] 2-methoxyethanol (3) Production of Zinc Oxide-Based Films Examples 10 to 17, Comparative Examples 11 to 20

Using the respective compositions obtained in Examples 2 to 9 and Comparative Examples 1 to 10, zinc oxide-based films were formed under conditions to be described hereinafter. To a glass substrate of 4 cm square heated at 200° C. on a hot plate, each composition was applied by a spray coater.

Furthermore, the haze and thickness of each formed film were also measured. The haze was measured by using the turbidity meter ("NDH2000", trade name, manufactured by Nippon Denshoku Industries Co., Ltd.). On the other hand, the thickness of the film was measured at a central part thereof by using an FE-SEM. The measurement results of haze and film thickness are shown in Tables 2 and 3.

TABLE 2

| | Composition for forming zinc oxide-based film | Homogeneity of film | Transmittance (%) | Resistivity (Ω · cm) | Haze (%) | Film thickness (nm) |
|---|---|---|---|---|---|---|
| Ex. 10 | Ex. 2 | Homogeneous | 90 | 243.2 | 31.8 | 195.3 |
| Ex. 11 | Ex. 3 | Homogeneous | 89.6 | 250.1 | 31.3 | 194.1 |
| Ex. 12 | Ex. 4 | Homogeneous | 79.7 | 59.1 | 31 | 192.6 |
| Ex. 13 | Ex. 5 | Homogeneous | 79.3 | 50.5 | 31.4 | 192.3 |
| Ex. 14 | Ex. 6 | Homogeneous | 80 | 58.9 | 31.2 | 193.3 |
| Ex. 15 | Ex. 7 | Homogeneous | 83.5 | 56.2 | 14.2 | 192.7 |
| Ex. 16 | Ex. 8 | Homogeneous | 82.7 | 62.8 | 14.8 | 193.3 |
| Ex. 17 | Ex. 9 | Homogeneous | 85.6 | 26 | 6.7 | 203 |

TABLE 3

| | Composition for forming zinc oxide-based film | Homogeneity of film | Transmittance (%) | Resistivity (Ω · cm) | Haze (%) | Film thickness (nm) |
|---|---|---|---|---|---|---|
| Comp. Ex. 11 | Comp. Ex. 1 | Irregular | 90.3 | ∞ | 21.5 | 201.1 |
| Comp. Ex. 12 | Comp. Ex. 2 | Irregular | 89.3 | ∞ | 23.5 | 193.1 |
| Comp. Ex. 13 | Comp. Ex. 3 | No film | — | — | — | — |
| Comp. Ex. 14 | Comp. Ex. 4 | Irregular | 86.8 | ∞ | 39.2 | 193.4 |
| Comp. Ex. 15 | Comp. Ex. 5 | Irregular | 88.7 | ∞ | 11.2 | 193.2 |
| Comp. Ex. 16 | Comp. Ex. 6 | Irregular | 83.2 | ∞ | 29.4 | 193.0 |
| Comp. Ex. 17 | Comp. Ex. 7 | Irregular | 87.8 | ∞ | 29.7 | 193.5 |
| Comp. Ex. 18 | Comp. Ex. 8 | Irregular | 83.7 | ∞ | 46.5 | 193.4 |
| Comp. Ex. 19 | Comp. Ex. 9 | Irregular | 87.5 | ∞ | 48.7 | 193.6 |
| Comp. Ex. 20 | Comp. Ex. 10 | Agglomerated | 87.7 | ∞ | 8.7 | 200.3 |

As shown in Tables 2 and 3, the use of the compositions obtained in Examples 2 to 9 was confirmed to be able to form homogeneous and transparent, zinc oxide-based films even when treated at 200° C. When the compositions obtained in Comparative Examples 1 to 10 were used, on the other hand, no good films were formed. Moreover, the resistivities of the formed films were unmeasurable high.

INDUSTRIAL APPLICABILITY

The use of the composition according to the present invention can easily form zinc oxide-based films useful, for example, as semiconductors, transparent conductors, light emitters, fluorescent emitters, photocatalysts, magnets, conductors, electrodes, high dielectrics, ferroelectrics, piezoelectrics, microwave dielectrics, optical waveguides, optical amplifiers, optical switches, electromagnetic shields, solar cells, and the like.

The invention claimed is:

1. A composition for forming a zinc oxide-based film, comprising, as essential components, a zinc compound represented by the following formula (1):

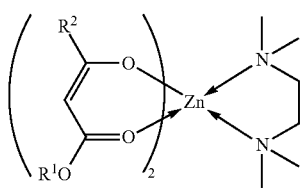

(1)

wherein $R^1$ and $R^2$ mutually independently represent an alkyl group having 1 to 4 carbon atoms, an ester solvent and/or alcohol solvent having a boiling point of 150° C. or lower, and N, N, N', N'-tetramethylethylenediamine; and 0.05 to 5 mass % of an acylacetate ester.

2. The composition according to claim 1, wherein $R^1$ and $R^2$ in the formula (1) are each a methyl group.

3. The composition according to claim 1, wherein the content of the zinc compound in the composition is 0.01 to 0.1 mol/L.

4. A process for producing a zinc oxide-based film, comprising the following steps:

applying the composition according to claim 3 to a substrate to form a coating layer, and treating the coating layer at 150 to 300° C. to convert the same into a film.

5. A process for producing a zinc oxide-based film, comprising the following steps:

applying the composition according to claim 1 to a substrate to form a coating layer, and treating the coating layer at 150 to 300° C. to convert the same into a film.

6. The process according to claim 5, wherein $R^1$ and $R^2$ in the formula (1) are each a methyl group.

* * * * *